(12) United States Patent
Aiden et al.

(10) Patent No.: US 11,618,923 B2
(45) Date of Patent: Apr. 4, 2023

(54) METHODS OF DETERMINING MULTIPLE INTERACTIONS BETWEEN NUCLEIC ACIDS IN A CELL

(71) Applicants: THE BROAD INSTITUTE, INC., Cambridge, MA (US); PRESIDENT AND FELLOWS OF HARVARD COLLEGE, Cambridge, MA (US)

(72) Inventors: Erez Lieberman Aiden, Houston, TX (US); Suhas Rao, Westwood, MA (US); Elena Stamenova, Reading, MA (US)

(73) Assignees: THE BROAD INSTITUTE, INC., Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/775,286

(22) PCT Filed: Mar. 14, 2014

(86) PCT No.: PCT/US2014/028921
§ 371 (c)(1),
(2) Date: Sep. 11, 2015

(87) PCT Pub. No.: WO2014/144491
PCT Pub. Date: Sep. 18, 2014

(65) Prior Publication Data
US 2016/0194710 A1 Jul. 7, 2016

Related U.S. Application Data

(60) Provisional application No. 61/793,557, filed on Mar. 15, 2013.

(51) Int. Cl.
*C12Q 1/68* (2018.01)
*C12Q 1/6883* (2018.01)
*C12Q 1/6876* (2018.01)

(52) U.S. Cl.
CPC ............ *C12Q 1/6883* (2013.01); *C12Q 1/68* (2013.01); *C12Q 1/6876* (2013.01); *C12Q 2600/158* (2013.01)

(58) Field of Classification Search
CPC ...... C12Q 1/68; C12Q 1/6883; C12Q 1/6876; C12Q 2600/158
See application file for complete search history.

(56) References Cited

U.S. PATENT DOCUMENTS

| | | |
|---|---|---|
| 2010/0062947 A1 | 3/2010 | De Laat et al. |
| 2010/0130373 A1 | 5/2010 | Dekker et al. |

FOREIGN PATENT DOCUMENTS

| | | |
|---|---|---|
| WO | 2004052080 A2 | 6/2004 |
| WO | 2005058931 A2 | 6/2005 |

(Continued)

OTHER PUBLICATIONS

Lieberman-Aiden et al. Science 2009; 326: 289-293.*

(Continued)

*Primary Examiner* — Angela M. Bertagna
(74) *Attorney, Agent, or Firm* — F. Brent Nix, Esq.; Johnson, Marcou, Isaacs & Nix, LLC

(57) ABSTRACT

Disclosed are methods for detecting spatial proximity relationships between nucleic acid sequences in a cell. The methods include: providing a sample of one or more cells comprising nucleic acids; fragmenting the nucleic acids present in the cells, wherein the fragmented nucleic acids have ends capable of joining to other fragmented nucleic acids; joining ends of fragmented nucleic acids to other ends fragmented nucleic acid to create at least one nucleic acid concatemer having at least one junction between the joined fragmented nucleic acids, and wherein the at least one nucleic acid concatemer encodes the information about the proximity of the DNA sequences in the cell; and determining the sequence at least one junction of the at least one nucleic (Continued)

acid concatemer, thereby detecting spatial proximity relationships between nucleic acid sequences in a cell.

12 Claims, 3 Drawing Sheets

(56) References Cited

FOREIGN PATENT DOCUMENTS

| WO | 2010036323 | A1 | 4/2010 |
|---|---|---|---|
| WO | 2012005595 | A2 | 1/2012 |
| WO | 2012135340 | A2 | 10/2012 |
| WO | 2012159025 | A2 | 11/2012 |

OTHER PUBLICATIONS

Duan et al. Nature 2010; 465: 363-367 (Year: 2010).*
Umbarger et al. Molecular Cell 2011; 44: 252-264 (Year: 2011).*
Duan et al. Nature 2010; 465: 363-367 + Supplementary Information (Year: 2010).*
International Search Report and Written Opinion dated Aug. 8, 2014 for PCT/2014/028921, Aug. 8, 2014, pp. 1-20.
Simonis, "Nuclear Organization of Active and Inactive Chromatin Domains Uncovered by Chromosome Conformation Capture-on-Chip (4C)", Nat. Genet., vol. 38, No. 11 (published online Oct. 8, 2006) Nov. 2006, pp. 1348-1354.
Extended European Search Report dated Nov. 3, 2016 for EPO Appl. No. 14764060.1, Nov. 3, 2016, 7 pages.
International Preliminary Report on Patentability dated Sep. 24, 2015 for PCT/US2014/028921, Sep. 24, 2015, 7 pages.
Sandhu, et al., "Chromatin Interaction Networks and Higher Order Architectures of Eukaryotic Genomes", Prospects, Journal of Cellular Biochemistry, vol. 112, No. 9, Aug. 18, 2011, 2218-2221.
Dolce, "European Office Action issued in Application No. 14764060.1 (Article 94(3))", dated Jan. 15, 2018, 1-5.
"Article 94(3) Office Action issued in EPO Application No. 14764060.1", dated Jul. 27, 2018, 1-4.
Celler, "Communication pursuant to Article 94(3) EPC, EP14764060.1, dated Jan. 22, 2019", 6 pages.
"Communication pursuant to Article 94(3) EPC", issued by the European Patent Office dated Mar. 15, 2021 for counterpart application No. 14764060.1.
"Communication under Rule 71(3)", issued by the European Patent Office for counterpart application No. EP14764060.1 dated Mar. 30, 2022.

* cited by examiner

FIG. 1 Protocol outline

FIG. 2
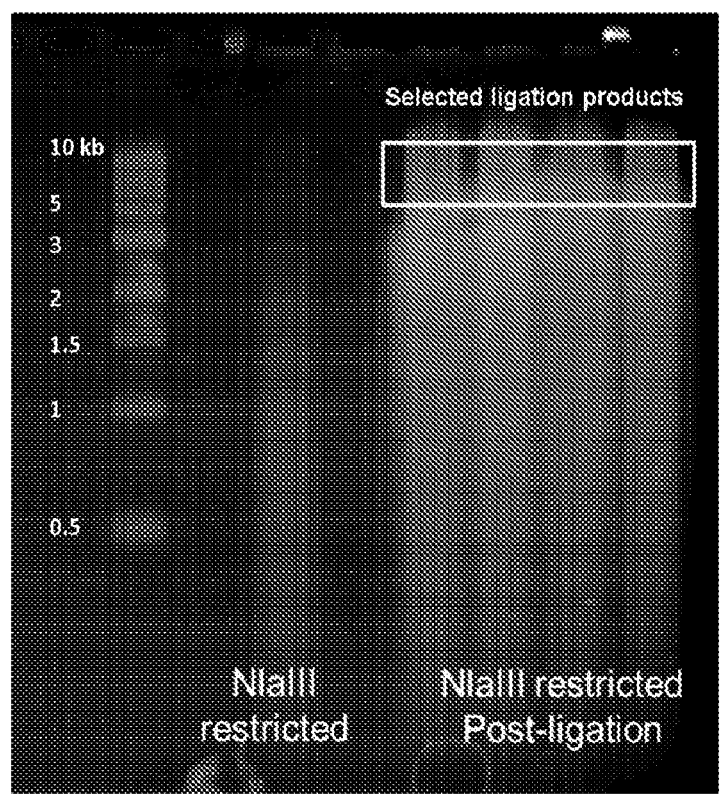
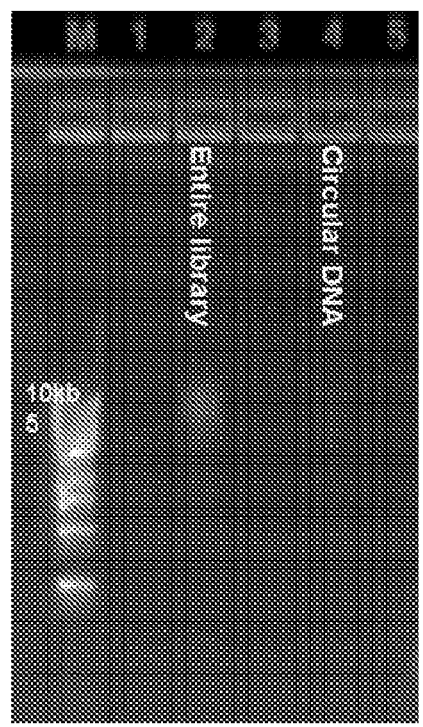

FIG. 3
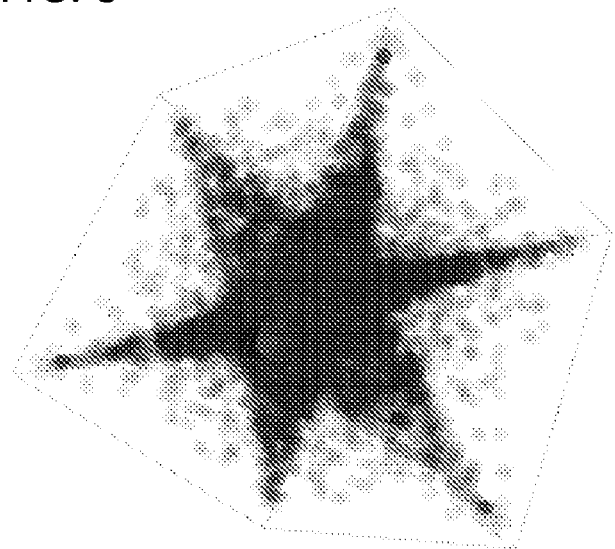
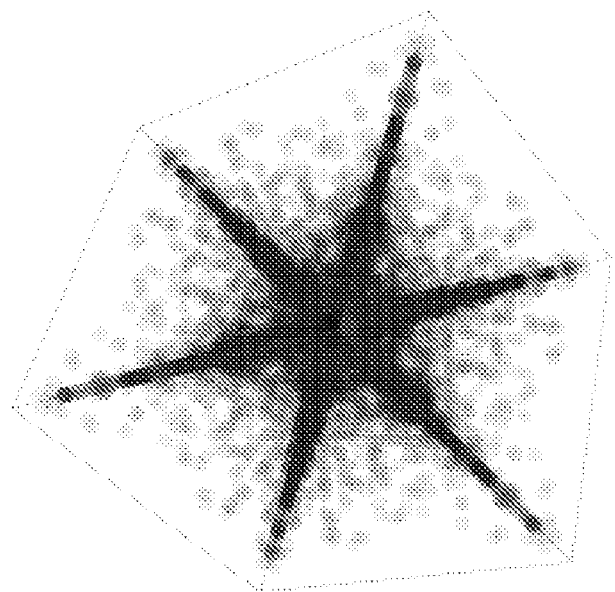

METHODS OF DETERMINING MULTIPLE INTERACTIONS BETWEEN NUCLEIC ACIDS IN A CELL

CROSS REFERENCE TO RELATED APPLICATION

This application is the U.S. National Stage of International Application No. PCT/US2014/028921, filed Mar. 14, 2014, published in English under PCT Article 21(2), which claims the priority benefit of the earlier filing date of U.S. Provisional Application No. 61/793,557, filed Mar. 15, 2013, which is hereby specifically incorporated herein by reference in its entirety.

STATEMENT OF GOVERNMENT SUPPORT

This invention was made with government support under Grant No. DP2OD008540, awarded by the National Institutes of Health. The government has certain rights in the invention.

FIELD OF THE DISCLOSURE

This disclosure concerns methods for simultaneously identifying multiple nucleic acid interactions in vivo.

BACKGROUND

A major goal in modern biology is defining the interactions between different biological actors in vivo. Over the past few decades, major advances have been made in developing methods to identify the molecular interactions with any given protein. With nucleic acids and in particular genomic DNA it is difficult to determine the interactions in a cell in part because of enormity, at the sequence level, of genomic DNA in a cell. It is believed that genomic DNA adopts a fractal globule state in which the DNA organized in three dimensions such that functionally related genomic elements, for example enhancers and their target genes, are directly interacting or are located in very close spatial proximity. Such close physical proximity between such elements is further believed to play a role in genome biology both in normal development and homeostasis and in disease. During the cell cycle the particular proximity relationships change, further complicating the study of genome dynamics. Understanding, and perhaps controlling, these tertiary interactions at the nucleic acid level has enormous potential to further our understating of the complexities cellular dynamics and perhaps fostering the development of new classes of therapeutics. Thus, methods are needed to investigate these interactions. This disclosure meets those needs.

SUMMARY OF THE DISCLOSURE

Disclosed are methods for detecting spatial proximity relationships between nucleic acid sequences. The methods include: providing a sample comprising nucleic acids, wherein the nucleic acids are fixed in position relative to one another; fragmenting the nucleic acids present in the cells, wherein the fragmented nucleic acids have ends capable of joining to other fragmented nucleic acids; joining ends of fragmented nucleic acids to other ends fragmented nucleic acid to create at least one nucleic acid concatemer having at least one junction between the joined fragmented nucleic acids, and wherein the at least one nucleic acid concatemer encodes the information about the proximity of the DNA sequences in the cell; and determining the sequence at least one junction of the at least one nucleic acid concatemer, thereby detecting spatial proximity relationships between nucleic acid sequences in a cell.

In some embodiments, the determining the sequence of the at least one junction of the nucleic acid concatemer includes nucleic acid sequencing. In some embodiments, determining the sequence of the at least one junction of the nucleic acid concatemer includes using a probe that specifically hybridizes to the at least one junction both 5' and 3' of the site of the at least one junction and spans the site of the at least one junction. In some embodiments, the method includes isolating the at least one nucleic acid concatemer, for example prior to sequence determination.

Also disclosed is a method for diagnosing a disease or condition. The method includes detecting, in a sample, one or more junctions in a nucleic acid concatemer that is indicative of a disease or condition, wherein detection of the one or more junctions in a nucleic acid concatemer that is indicative of a disease or condition diagnoses the disease or condition.

Also disclosed are nucleic acid concatemers that include at least one junction wherein the nucleic acid concatemer encodes the information about the proximity of the DNA and/or RNA, as well as amplification products and probes for detecting such nucleic acids.

The foregoing and other features of this disclosure will become more apparent from the following detailed description of a several embodiments, which proceeds with reference to the accompanying figures.

BRIEF DESCRIPTION OF THE FIGURES

FIG. 2 is a set of digital images of DNA gels showing the result of the methods disclosed herein. The individual gels represent the results of discrete steps in method and verify the presence of the expected complexes. Library prepared using 12 million formaldehyde-crosslinked human lymphoblastoid cells (GM 12878) yielded 2 µg DNA of 5-10 kb size (mostly linear ligation products).

FIG. 3 is a set of multidimensional contact maps, showing triple contacts between DNA in a cell. This result demonstrates that the disclosed methods can map multiple contacts as represented by a multidimensional contact map.

DETAILED DESCRIPTION OF SEVERAL EMBODIMENTS

I. Summary of Terms

Figure 1:
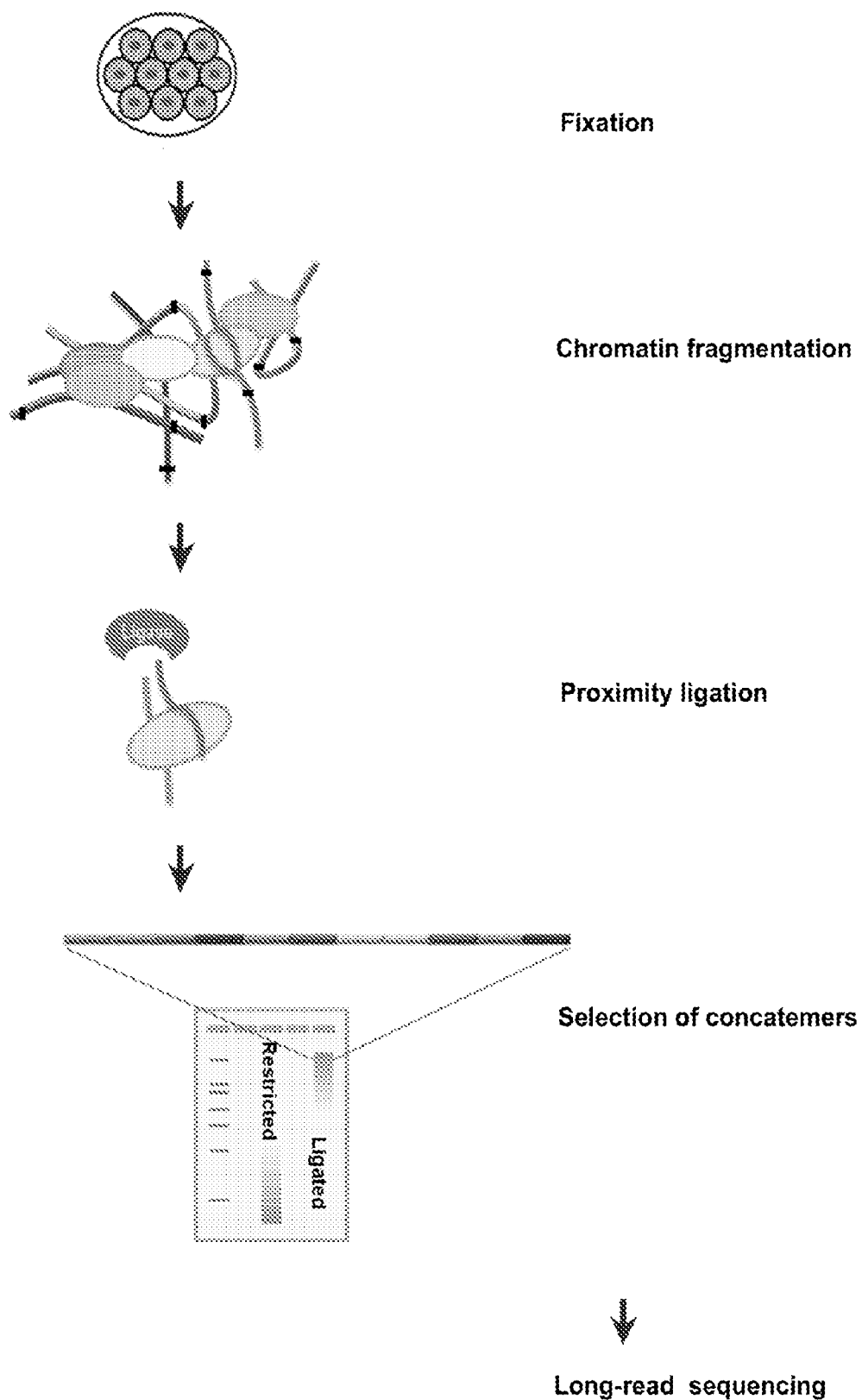
FIG. 1 is a schematic showing an overview of an exemplary COLA procedure.

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises"

means "includes." In case of conflict, the present specification, including explanations of terms, will control.

To facilitate review of the various embodiments of this disclosure, the following explanations of specific terms are provided:

Amplification: To increase the number of copies of a nucleic acid molecule. The resulting amplification products are called "amplicons." Amplification of a nucleic acid molecule (such as a DNA or RNA molecule encoding targeting probe or DNA concatemer) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR (rt PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Binding or stable binding (of an oligonucleotide): An oligonucleotide, such as a nucleic acid probe that specifically binds to a junction in a nucleic acid concatemer, binds or stably binds to a target nucleic acid, such as nucleic acid concatemer, if a sufficient amount of the oligonucleotide forms base pairs or is hybridized to its target nucleic acid. Binding can be detected by either physical or functional properties.

Binding site: A region on a protein, DNA, or RNA to which other molecules stably bind. In one example, a binding site is the site on a nucleic acid concatemer.

Contacting: Placement in direct physical association, including both in solid or liquid form, for example contacting a sample with a nucleic acid probe and/or a crosslinking agent.

Conditions sufficient to detect: Any environment that permits the desired activity, for example, that permits a probe to detect a target nucleic acid sequence, such as a DNA concatemer.

Control: A reference standard. A control can be a known value or range of values indicative of basal levels or amounts or present in a tissue or a cell or populations thereof. A control can also be a cellular or tissue control, for example a tissue from a non-diseased state and/or exposed to different environmental conditions. A difference between a test sample and a control can be an increase or conversely a decrease. The difference can be a qualitative difference or a quantitative difference, for example a statistically significant difference.

Covalently linked: Refers to a covalent linkage between atoms by the formation of a covalent bond characterized by the sharing of pairs of electrons between atoms. In one example, a covalent link is a bond between an oxygen and a phosphorous, such as phosphodiester bonds in the backbone of a nucleic acid strand. In another example, a covalent link is one between a target nucleic acid and a protein and/or nucleic acid that has been crosslinked to the target nucleic acid by chemical means. In another example, a covalent link is one between fragmented nucleic acids to create a nucleic acid concatemer.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Concatemer: A long continuous nucleic acid molecule that contains three or more copies of the fragmented nucleic sequences linked in series. A concatemer can be RNA, DNA or both RNA and DNA, linked together.

Crosslinking agent: A chemical agent, or even light, facilitating the attachment of one molecule to another molecule. Crosslinking agents can be protein-nucleic acid crosslinking agents, nucleic acid-nucleic acid crosslinking agents, and protein-protein crosslinking agents. Examples of such agents are known in the art. In some embodiments, a crosslinking agent is a reversible crosslinking agent. In some embodiments, a crosslinking agent is a non-reversible crosslinking agent.

Detect: To determine if an agent (such as a signal or particular nucleic acid, such as a DNA concatemer, or protein) is present or absent. In some examples, this can further include quantification in a sample, or a fraction of a sample, such as a particular cell or cells within a tissue. Detection can be direct or indirect, for example through the detection of an amplification product of a DNA concatemer.

Detectable label: A compound or composition that is conjugated directly or indirectly to another molecule to facilitate detection of that molecule. Specific, non-limiting examples of labels include fluorescent tags, enzymatic linkages, and radioactive isotopes. In some examples, a label is attached to an antibody or nucleic acid to facilitate detection of the molecule antibody or nucleic acid specifically binds. In some examples, a detectable label can be used to isolate or purify a molecule to which it is attached, either directly or indirectly.

DNA sequencing: The process of determining the nucleotide order of a given DNA molecule. Generally, the sequencing can be performed using automated Sanger sequencing (ABI3730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

In some embodiments, DNA sequencing is performed using a chain termination method developed by Frederick Sanger, and thus termed "Sanger based sequencing" or "SBS." This technique uses sequence-specific termination of a DNA synthesis reaction using modified nucleotide substrates. Extension is initiated at a specific site on the template DNA by using a short oligonucleotide primer complementary to the template at that region. The oligonucleotide primer is extended using DNA polymerase in the presence of the four deoxynucleotide bases (DNA building blocks), along with a low concentration of a chain terminating nucleotide (most commonly a di-deoxynucleotide). Limited incorporation of the chain terminating nucleotide by the DNA polymerase results in a series of related DNA fragments that are terminated only at positions where that particular nucleotide is present. The fragments are then size-separated by electrophoresis a polyacrylamide gel, or in a narrow glass tube (capillary) filled with a viscous polymer. An alternative to using a labeled primer is to use labeled terminators instead; this method is commonly called "dye terminator sequencing."

"Pyrosequencing" is an array based method, which has been commercialized by 454 Life Sciences. In some embodiments of the array-based methods, single-stranded DNA is annealed to beads and amplified via EmPCR®. These DNA-bound beads are then placed into wells on a fiber-optic chip along with enzymes that produce light in the presence of ATP. When free nucleotides are washed over this chip, light is produced as the PCR amplification occurs and ATP is generated when nucleotides join with their complementary base pairs. Addition of one (or more) nucleotide(s) results in a reaction that generates a light signal that is recorded, such as by the charge coupled device (CCD) camera, within the instrument. The signal strength is proportional to the number of nucleotides, for example, homopolymer stretches, incorporated in a single nucleotide flow.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcoumarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (TEXAS RED); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

High throughput technique: Through a combination of robotics, data processing and control software, liquid handling devices, and detectors, high throughput techniques allows the rapid screening of potential reagents, conditions, or targets in a short period of time, for example in less than 24, less than 12, less than 6 hours, or even less than 1 hour. Through this process, one can rapidly identify active compounds, antibodies, or genes affecting a particular binding event.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide (or it's analog) and the DNA, RNA, and or DNA-RNA hybrid target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Isolated: An "isolated" biological component (such as a protein, a nucleic acid, such as the probes and concatemer nucleic acids described herein) has been substantially separated or purified away from other biological components in the cell of the organism in which the component naturally occurs, for example, extra-chromatin DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Junction: The site where two nucleic acid fragments or joined, for example using the methods described herein. A junction encodes information about the proximity of the nucleic acid fragments that participate in formation of the junction. For example, junction formation between to nucleic acid fragments indicates that these two nucleic acid sequences where in close proximity when the junction was formed, although they may not be in proximity in liner nucleic acid sequence space. Thus, a junction can define ling range interactions.

Nucleic acid (molecule or sequence): A deoxyribonucleotide or ribonucleotide polymer including without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties, and modified phosphate backbones, for example as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethyl-aminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Targeting Probe: A probe, such as a targeting probe, includes an isolated nucleic acid capable of hybridizing to a target nucleic acid, such as a DNA concatemer. In some examples a targeting probe includes a detectable label, such as biotin, attached to a nucleic acid molecule. In some examples, a targeting probe spans at least one junction of a DNA concatemer.

Sample: A sample, such as a biological sample, that includes biological materials (such as nucleic acid and proteins, for example double-stranded nucleic acid binding proteins) obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ.

Specific Binding Agent: An agent that binds substantially or preferentially only to a defined target such as a protein, enzyme, polysaccharide, oligonucleotide, DNA, RNA, recombinant vector or a small molecule. In an example, a "capture moiety specific binding agent" is capable of binding to a capture moiety that is covalently linked to a targeting probe.

A nucleic acid-specific binding agent binds substantially only to the defined nucleic acid, such as a DNA concatemer, or to a specific region within the nucleic acid, such as a junction. In some embodiments a specific binding agent is a targeting probe, that specifically binds to a target nucleic acid of interest.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Test agent: Any agent that that is tested for its effects, for example its effects on a cell and/or interaction profile of a target nucleic acid of interest. In some embodiments, a test agent is a chemical compound, such as a chemotherapeutic agent, antibiotic, or even an agent with unknown biological properties.

Tissue: A plurality of functionally related cells. A tissue can be a suspension, a semi-solid, or solid. Tissue includes cells collected from a subject such as blood, cervix, uterus, lymph nodes breast, skin, and other organs.

Under conditions that permit binding: A phrase used to describe any environment that permits the desired activity, for example conditions under which two or more molecules, such as nucleic acid molecules and/or protein molecules, can bind. In some embodiments, conditions that permit binding are highly denaturing conditions.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting II. Description of Several Embodiments Disclosed herein is a method for detecting spatial proximity relationships between nucleic acids, such as RNA and DNA in vivo by joining together nucleic acids that have been fragment. The fragmented nucleic acids are joined by virtue of their proximity in space to form large nucleic acid concaeters that include multiple junctions, each of which contains information about the spatial proximity relationship of the fragments making up the concatemer and hence the larger nucleic acid from which the fragment was derived. Because the DNA concatemers formed using the disclosed method include multiple junctions, the method termed "COncatamer Ligation Assay" (COLA), can simultaneously map substantially all of the interactions of nucleic acids in a cell, including spatial arrangements of DNA and RNA in cell. While specific examples have been shown for DNA, the methods disclosed herein are equally applicable to RNA in a cell, and in some circumstances, mapping the interactions of both RNA and DNA in a cell, for example individually (i.e. DNA-DNA interactions and RNA-RNA interactions), concurrently, or even cross nucleic acid type interactions (i.e. RNA-DNA interactions). An exemplary schematic of the method is shown in FIG. 1. By mapping the sequences contributing to the concatemers to the known nucleic acids in a cell, information about which nucleic acid sequence or in close proximity to other nucleic acid in a cell can be gleaned. In addition, because the concatemers include multiple nucleic acid fragments linked together, each concatemer includes multiple junctions that encode information about the spatial relationships amongst multiple sequence elements. For example, consider a concatemer of nucleic acid fragments A, B, C, D, E, and F in sequence A-B-C-D-E-F, where the letters represent nucleic acid sequences that are not very close in liner sequence space. If such a concatemer is detected, it is known that all of these nucleic acid sequences is in close proximity, likely with those making direct junctions being in closer proximity than those with interviewing sequence between them. Thus rather than getting a pair wise proximity map, the current technology enables the formation of proximity maps or greater complexity. If one next considers the concatemer of nucleic acid fragments G, H, C, D, I, J, and K in sequence G-H-C-D-I-J-K, where the letters represent nucleic acid sequences that are not very close in liner sequence space, once can see that the two concatemers overlap, which would suggest that the sequences in G, H, I, J and K where in close proximity to the sequences C and D but not necessarily to the sequences A, B, E, and F. Once can immediately appreciate that analysis of such concatemers can be used to build a three dimensional map of the nucleic acids in a cell. The depth of contacts leads to a multidimensional contact map, such as a three, four or more dimensional or more map, that describes all contacts between DNA sequences in a cell. By way of example, for three pieces of DNA that are in contact can be used to build a three dimensional map of DNA in a cell (see FIGS. 3A-3C). The ability of the present methods to allow one to determine multiple contacts simultaneously is a large improvement over other technologies that can at best determine pairwise contacts.

A. COncatamer Ligation Assay (COLA)

The disclosed methods include providing a sample of one or more cells, nuclear extract, cellular milieu or system of nucleic acids or interest that include nucleic acids. In some examples, the sample is a sample of permeablized nuclei, mulple nuclei, isolated nuclei, synchronized cells, (such at various points in the cell cycle, for example metaphase) or acellular. In some embodiments, the nucleic acid are held in a fixed position relative to each other, such the proximity information about nucleic acids is in the samples, such as a sample of one or more cells is locked in, for example crosslinked or otherwise stabilized, for example by use of an agent such as agar that keeps the positions of the substituents in the sample from moving relative to each other in a appreciable degree. For example, a sample of cells can be treated with a crosslinker to lock in the spatial information or relationship about the molecules in the cells, such as the DNA and RNA in the cell. In another example, a sample is coated in agar. In some embodiments, the spatial relation the nucleic acids are fixed in position relative to one another. Any method of fixing the nucleic acids in their positions can be used. In some embodiments, the cells are fixed, for example with a fixative, such as an aldehyde, for example formaldehyde or gluteraldehyde. In some embodiments, a sample of one or more cells is crosslinked with a crosslinker to maintain the spatial relationships in the cell. For example, a sample of cells can be treated with a crosslinker to lock in the spatial information or relationship about the molecules in the cells, such as the DNA and/or RNA in the cell. In other embodiments, the relative positions of the nucleic acid can be maintained with out using crosslinking agents. For example the nucleic acids can be stabilized using spermine and spermidine (see Cullen et al., Science 261, 203 (1993)), which is specifically incorporated herein by reference in its entirety). Other methods of maintaining the positional relationships of nucleic acids are known in the art.

In some embodiments, the nucleic acids present in the sample are fragmented to release ands of the nucleic acids that are capable of being joined together. The fragmentation can be done by a variety of methods, such as enzymatic and chemical cleavage as well as mechanical shearing, base hydrolysis, acid hydrolysis, or heat-induced thermal destabilization. For example, RNA can be fragmented using an RNAase that cuts at specific sequences of RNA, thereby yielding fragmented RNA. Suitable Rnases are commercially available, for example form New England Biolabs. One of ordinary skill in the art can choose the Rnase, with out undue experimentation. Similarly, the DNA, such as chromatin bound DNA can be fragmented with one or more restriction enzymes. Suitable restriction enzymes are commercially available, for example form New England Biolabs. One of ordinary skill in the art can choose the restriction enzyme with out undue experimentation. One of ordinary skill in the art will appreciate that using different fragmentation techniques, such as different enzymes with different sequence requirements, will yield different fragmentation patterns and therefore different DNA and/or RNA ends. If both DNA and RNA is to be analyzed, the DNA and RNA fragmentation can be done simultaneously, or stepwise. For example, the DNA can be fragmented before the RNA, or conversely, the RNA can be fragmented before the DNA. The choice of order is typically dictated by the reagents and/or methods used to fragment the DNA and RNA. One of ordinary skill in the art can choose the order based on the reagents used, with out undue experimentation. Because the spatial relationships are locked in the nucleic acids, the free ends of the fragmented nucleic acids are able to join together with nucleic acids in close proximity. In some embodiments the nucleic acids are DNA and/or RNA.

Typically, the nucleic acid fragments are desired to be between about 100 and about 1000 bases in length, although longer and shorter fragments are contemplated. In some embodiments, the nucleic acid fragments are between about 100 and about 1000 bases in length, such as about 100, about 150, about 200, about 250, about 300, about 350, about 400, about 450, about 500, about 550, about 600, about 650, about 700, about 750, about 800, about 850, about 900, about 950 or about 1000 bases in length, for example form about 100 to about 1000, about 200 to about 800, about 500 to about 850, about 100 to about 500 and about 300 to about 775 base pairs in length and the like.

The process of fragmenting the DNA and/or RNA in the sample can yield ends that are capable of being joined. However, in some circumstances, the ends of the RNA and/or DNA are not competent for joining after fragmentation. Thus, in some embodiments, the ends of the RNA and/or DNA are repaired to yield ends capable of being joined. End repair can be accomplished by a variety of techniques available to one of ordinary skill in the art. It is further contemplated that the fragmentation and end repair of one type of nucleic acid, such as one of RNA or DNA, can occur prior to the digestion and/or end repair of the second type of nucleic acid.

The ends of fragmented nucleic acids are joined to other ends fragmented nucleic acid to create at least one nucleic acid concatemer having at least one junction between the joined fragmented nucleic acids. The at least one nucleic acid concatemer encodes the information about the proximity of the DNA sequences in the cell based on the sequence of the nucleic acids on each side of the junction. Is some embodiments are least 2 junctions or formed, such as at least 3, 4, 5, 6, 7, 8, 9, 10, 11, 12, 13, 14, 15, 20, 25, 30, 35, 40, 45, 50, 100, 150, 200, 300, 400, 500, 600, 700, 800, 900, 1000 or more. While the number of junctions that could possibly form in a single concatemer is exceedingly large, in that all of the nucleic acid present in the cell could form one concatemer, this is unlikely. Thus, in some embodiments, the number of junctions is less than about 1,000,000, such as less than about 100,000, 10,000, 5,000, 1,000, 100, 50, 20, 10, 9, 8, 7, 6, 5, or 4.

In some embodiments the sequence of at least one junction of the at least one nucleic acid concatemer is determined, thereby detecting spatial proximity relationships between nucleic acid sequences in a cell. In some embodiments, the nucleic acid concatemer is DNA, RNA or a combination thereof.

In some embodiments, determining the sequence of a target junction DNA molecule includes using a probe that specifically binds to the target junction DNA molecule at the site of the junction. In particular embodiments, the probe specifically hybridizes to the target junction both 5' and 3' of the site of the junction and spans the site of the junction. A probe that specifically binds to the target join DNA molecule at the site of the join can be selected based on known interactions, for example in a diagnostic setting where the presence of a particular target junction, or set of target junctions, has been correlated with a particular disease or condition. It is further contemplated that once a target join is known, a probe for that target join can be synthesized.

In some embodiments, the nucleic acid concatemers are isolated, for example prior to sequence analysis. In some embodiments the isolated concatemers are at least about 500 base pairs in length, such as about 500, 600, 700, 800, 900, 1,000, 2,000, 5,000, 1,0000, 2,0000 50,000, or a 100,000 base pairs in length or more. In some embodiments, the isolated concatemers is less than about 1,000,000 base pairs in length, such as less than about 100,000, 10,000, 5,000, or 1,000 base pairs in length.

In some embodiments, no junction marker is used to mark the junction. In some embodiments the nucleic acid concatemers are not subjected to secondary fragmentation. In some embodiments, the location of the at least one junction is identified relative to chromosomal location.

In some embodiments, the cells are lysed to release the cellular contents, for example after crosslinking. In some examples the nuclei are lysed as well, while in other examples, the nuclei are maintained intact, which can then be isolated and optionally lysed, for example using an reagent that selectively targets the nuclei or other separation technique known in the art.

In some embodiments of the disclosed methods, the cells or contacted with a crosslinking agent to provide the cross-linked cells. In some examples, the cells are contacted with a protein-nucleic acid crosslinking agent, a nucleic acid-nucleic acid crosslinking agent, a protein-protein crosslinking agent or any combination thereof. By this method, the RNA and DNA present in the sample become resistant to special rearrangement and the spatial information about the DNA and RNA in the cell is maintained. In some examples, a crosslinker is a reversible crosslinker, such that the cross-linked molecules can be easily separated in subsequent steps of the method. In some examples, a crosslinker is a non-reversible crosslinker, such that the crosslinked molecules cannot be easily separated. In some examples, a crosslinker is light, such as UV light. In some examples, a cross linker is light activated. These crosslinkers include formaldehyde, disuccinimidyl glutarate, UV-254, psoralens and their derivatives such as aminomethyltrioxsalen, glutaraldehyde, ethylene glycol bis[succinimidylsuccinate], bissulfosuccinimidyl suberate, 1-Ethyl-3-[3-dimethylaminopropyl]carbodiimide (EDC) bis[sulfosuccinimidyl] suberate ($BS^3$) and other compounds known to those skilled in the art, including those described in the *Thermo Scientific Pierce Crosslinking Technical Handbook,* Thermo Scientific (2009) as available on the world wide web at piercenet.com/files/1601673_Crosslink_HB_Intl.pdf.

The disclosed methods are also particularly suited to monitoring disease states, such as disease state in an organism, for example a plant or an animal subject, such as a mammalian subject, for example a human subject. Certain disease states may be caused and/or characterized by the differential formation of certain junctions in a concatemer. For example, certain interactions may occur in a diseased cell but not in a normal cell. In other examples, certain interactions may occur in a normal cell but not in diseased cell. Thus, using the disclosed methods a profile of the special relationships of nucleic acids in vivo, can be correlated with a disease state. The junction profile correlated with a disease can be used as a "fingerprint" to identify and/or diagnose a disease in a cell, by virtue of having a similar "fingerprint." In addition, the profile can be used to monitor a disease state, for example to monitor the response to a therapy, disease progression and/or make treatment decisions for subjects.

The ability to obtain an interaction profile allows for the diagnosis of a disease state, for example by comparison of the profile present in a sample with the correlated with a specific disease state, wherein a similarity in profile indicates a particular disease state.

Accordingly, aspects of the disclosed methods relate to diagnosing a disease state based on a junction profile correlated with a disease state, for example cancer, or an infection, such as a viral or bacterial infection. It is understood that a diagnosis of a disease state could be made for any organism, including without limitation plants, and animals, such as humans.

Aspects of the present disclosure relate to the correlation of an environmental stress or state with junction profile, such as a sample of cells, for example a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value.

In some embodiments, the disclosed methods can be used to screen chemical libraries for agents that modulate nucleic acid interaction profiles, for example that alter the interaction profile from an abnormal one, for example correlated to a disease state to one indicative of a disease free state. By exposing cells, or fractions thereof, tissues, or even whole animals, to different members of the chemical libraries, and performing the methods described herein, different members of a chemical library can be screened for their effect on interaction profiles simultaneously in a relatively short amount of time, for example using a high throughput method.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

Appropriate agents can be contained in libraries, for example, synthetic or natural compounds in a combinatorial library. Numerous libraries are commercially available or can be readily produced; means for random and directed synthesis of a wide variety of organic compounds and biomolecules, including expression of randomized oligonucleotides, such as antisense oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

The compounds identified using the methods disclosed herein can serve as conventional "lead compounds" or can themselves be used as potential or actual therapeutics. In some instances, pools of candidate agents can be identified and further screened to determine which individual or sub-pools of agents in the collective have a desired activity.

Appropriate samples for use in the methods disclosed herein include any conventional biological sample obtained from an organism or a part thereof, such as a plant, animal, and the like. In particular embodiments, the biological sample is obtained from an animal subject, such as a human subject. A biological sample is any solid or fluid sample obtained from, excreted by or secreted by any living organism, including without limitation, single celled organisms, such as yeast, protozoans, and amebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as a rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al., *NEJM* 318:589-93 (1988); and Ognibene et al., *Am. Rev. Respir. Dis.* 129:929-32 (1984).

This disclosure also provides integrated systems for high-throughput testing, or automated testing. The systems typically include a robotic armature that transfers fluid from a source to a destination, a controller that controls the robotic armature, a detector, a data storage unit that records detection, and an assay component such as a microtiter dish comprising a well having a reaction mixture for example media.

In some embodiments of the disclosed methods, determining the identity of a nucleic acid, such as a target join, includes detection by nucleic acid hybridization. Nucleic acid hybridization involves providing a probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. In some examples, RNA is detected using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992).

In one embodiment, the hybridized nucleic acids are detected by detecting one or more labels attached to the sample nucleic acids. The labels can be incorporated by any of a number of methods. In one example, the label is simultaneously incorporated during the amplification step in the preparation of the sample nucleic acids. Thus, for example, polymerase chain reaction (PCR) with labeled primers or labeled nucleotides will provide a labeled amplification product. In one embodiment, transcription amplification, as described above, using a labeled nucleotide (such as fluorescein-labeled UTP and/or CTP) incorporates a label into the transcribed nucleic acids.

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

Means of detecting such labels are also well known. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N. Y., 1993).

In some embodiments, the identity of a nucleic acid is determined by DNA or RNA sequencing. Generally, the sequencing can be performed using automated Sanger sequencing (AB13730x1 genome analyzer), pyrosequencing on a solid support (454 sequencing, Roche), sequencing-by-synthesis with reversible terminations (ILLUMINA® Genome Analyzer), sequencing-by-ligation (ABI SOLiD®) or sequencing-by-synthesis with virtual terminators (HELISCOPE®).

Examples of information that can be obtained form the disclosed methods and the analysis of the results thereof, include without limitation, 3 dimensional genome mapping, genome assembly, one dimensional genome mapping, the use of single nucleotide polymorphisms to phase genome maps, for example to determine the patterns of chromosome inactivation, such as for analysis of genomic imprinting.

B. Concatemers and Probes

Also disclosed are isolated nucleic acid concatemers and amplification products thereof, such as RNA, DNA or a combination thereof. A nucleic acid concatemer includes at least one junction that encodes information about the proximity of nucleic acid sequences in a cell, for example as formed by the methods disclosed herein. The presence of a specific junction in a nucleic acid concatemer can be correlated with a disease state or environmental condition. For example, certain disease states may be caused and/or characterized by the differential formation of certain junctions. Similarly a specific junction in a nucleic acid concatemer can be correlated to an environmental stress or state, such as but not limited to heat shock, osmolarity, hypoxia, cold, oxidative stress, radiation, starvation, a chemical (for example a therapeutic agent or potential therapeutic agent) and the like.

This disclosure also relates, to isolated nucleic acid probes that specifically bind to target a specific junction in a nucleic acid concatemer, such as a junction indicative of a disease state or environmental condition. To recognize a junction, a probe specifically hybridizes to the target join both 5' and 3' of the site of the junction and spans the site of the join. In some embodiments, the probe is labeled, such as radiolabeled, fluorescently-labeled, biotin-labeled, enzymatically-labeled, or chemically-labeled. Non-limiting examples of the probe is an RNA probe, a DNA probe, a locked nucleic acid (LNA) probe, or a hybrid RNA-DNA probe. Also disclosed are sets of probes for binding to a junction, as well as devices, such as nucleic acid arrays for detecting a junction.

In embodiments, the total length of the probe, including end linked PCR or other tags, is between about 10 nucleotides and 200 nucleotides, although longer probes are contemplated. In some embodiments, the total length of the probe, including end linked PCR or other tags, is at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 191, 192, 193, 194, 195, 196, 197, 198, 199 or 200.

In some embodiments the total length of the probe, including end linked PCR or other tags, is less then about 2000 nucleotides in length, such as less than about 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 500, 750, 1000, 1250, 1500, 1750, 2000 nucleotides in length or even greater. In some embodiments, the total length of the probe, including end linked PCR or other tags, is between about 30 nucleotides and about 250 nucleotides, for example about 90 to about 180, about 120 to about 200, about 150 to about 220 or about 120 to about 180 nucleotides in length. In some embodiments, a set of probes is used to target a specific target junction or a set of target junctions.

In some embodiments, the probe is detectably labeled, either with an isotopic or non-isotopic label, alternatively the target join or amplification product thereof is labeled. Non-isotopic labels can, for instance, comprise a fluorescent or luminescent molecule, biotin, an enzyme or enzyme substrate or a chemical. Such labels are preferentially chosen such that the hybridization of the probe with target join can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor.

An array containing a plurality of heterogeneous probes for the detection of target junction in a concatemer are disclosed. Such arrays may be used to rapidly detect and/or identify the target junction in a concatemer present in a sample, for example as part of a diagnosis. Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

Any sample potentially containing, or even suspected of containing, target junction may be used. A hybridization signal from an individual address on the array indicates that the probe hybridizes to a nucleotide within the sample. This system permits the simultaneous analysis of a sample by plural probes and yields information identifying the target junction contained within the sample. In alternative embodiments, the array contains target junction and the array is contacted with a sample containing a probe. In any such embodiment, either the probe or the target junction may be labeled to facilitate detection of hybridization.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

Examples of substrates for the phage arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+96-well plate, or the 384 Microlite+384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

C. Kits

The nucleic acid probes and other reagents disclosed herein for use in the disclosed methods can be supplied in the form of a kit. In such a kit, an appropriate amount of one or more of the nucleic acid probes is provided in one or more containers or held on a substrate. A nucleic acid probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection, of a target junction in a concatemer. The amount of nucleic acid probe supplied in the kit can be any appropriate amount, and may depend on the target market to which the product is directed. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In some embodiments, kits also may include the reagents necessary to carry out methods disclosed herein. In other particular embodiments, the kit includes equipment, reagents, and instructions for the methods disclosed herein.

The following examples are provided to illustrate certain particular features and/or embodiments. These examples should not be construed to limit the invention to the particular features or embodiments described.

EXAMPLES

Example 1

Protocol for Preparation of Concatemer Library for Long-Read Sequencing

Lysis and Restriction Digest
1) To lyse the cells, lysis buffer (500 μl 10 mM Tris-HCl pH8.0, 10 mM NaCl, 0.2% IGEPAL CA630) is mixed with 100 μl protease inhibitors and added to one formaldehyde-crosslinked pellet (5-20 million cells).
2) Incubate cell suspension on ice for >15 minutes.
3) Centrifuge for 5 minutes at 2500×G at RT, discard the supernatant. Next steps are based on 5 million cells per tube.
4) Wash nuclear pellet in 1× restriction buffer by spinning at 2500×G at RT
5) To facilitate complete cell lysis and solubilization of proteins, resuspend pellet is 50 ul of 0.5% SDS, add and heat at 62 C for 10 min. After heating is over, add 150 ul water and 25 ul 10% TRITON X-100 to quench SDS and mix well avoiding excessive foaming. Incubate at 37 C for 15 min.
6) Add 25 ul 10× restriction buffer.
7) Chromatin is subsequently digested overnight at 37° C. by adding 400 Units of NlaIII restriction enzyme. Rotate tubes while incubating.

Proximity Ligation
1) Inactivate restriction enzyme by heating at 62 C for 20 min.
2) To each tube add 900 ul of master mix:
   662 ul water (total volume of ligation reaction is 1.2 ml)
   120 ul 10×NEB ligation buffer (B0202S)
   100 ul TritonX 10%
   12 ul BSA (10 mg/ml)
   5 ul T4 DNA ligase (400 U/ul)
   1 ul RNase cocktail
3) Mix by inverting the tubes and incubate all tubes for 4 hours at room temperature, while rotating them.

Cross-Link Reversal and Purification
1) Crosslinks are reversed and protein is degraded by adding to each tube 50 μl 20 mg/ml proteinase K and 120 ul 10% SDS incubating the tubes first for 30 min at 55° C. Add 130 ul 5M NaCl and incubate at 68-70 C for at least 2 hours or overnight whatever fits protocol schedule.
2) Cool the reaction mixtures to room temperature (do not cool on ice) split to 2×2 ml tubes. Precipitate with 1.2 ml pure ethanol and 100 ul of 3M Na-acetate, pH 5.2. Mix and incubate at −80 for 15 min. Spin at max speed for 15 min at 2 C (SDS becomes insoluble at low temperature and serves as a DNA-carrier during the spin).
3) Immediately after spinning, carefully remove (DO NOT pour off, pellets may become loose) the supernatant. Leave tubes at RT for few minutes so SDS becomes soluble. Resuspend in 800 ul 70% ethanol. Spin at max speed for about 5 mins. Remove all supernatant and wash pellet twice with 70% ethanol. Dissolve pellet in 50 ul 1× Tris low EDTA buffer or EB buffer and incubate at 37 C for 15 min to fully dissolve DNA.

Selection and Recovery of Ligation Products

Chromatin restricted with NlaIII, is under 3 kb in size. Post-ligation DNA in the range 5-10 kb can be selected thus enriching ligation products. Since the size of the fragments is relatively big, they are selected by using gel electrophoresis followed by β-Agarase I digestion of the gel. β-Agarase I digests agarose, releasing trapped DNA and producing carbohydrate oligos which can no longer gel.

Selection and Recovery of Ligation Products

1) Prepare 1% agarose gel in 1× Tris-acetate EDTA (TAE) buffer: Dissolve 1.5 g low-melting point agarose (SEAPLAQUE GTG or NUSIEVE GTG agarose also could be used) in 150 ml of TAE in a loosely capped media bottle and microwave for 1 min. Heat for 1 more min or until agarose is fully dissolved. Open cap and let solution stay at room temperature for couple of minutes. Carefully pour the agarose in the gel casting tray with a wide comb. Leave the gel to solidify at room temperature.
2) Submerge gel in 1×TAE running buffer in the electrophoresis chamber and add 1 kb NEB Quickload ladder to the first well. Add 10 ul of 6× loading dye to the DNA library. Mix by pipetting and skipping the well next to the ladder, load 20 ul DNA in next wells. Run for 2 hours at 100V.
3) Stain the gel in 100 ul water with 10 ul SYBR green for 20 min.
4) Visualize DNA with a Gel-Doc and take an image. Ligated DNA is expected to run higher than 3 kb.
5) Move to a dark room and transfer the gel to a disposable Gel-Hand sheet. Visualize it on DarkReader and excise DNA fragments between 5-10 k base pairs.
6) Transfer gel pieces to a labeled tube using clean toothpick or a pipet tip.
7) Equilibrate the DNA-containing agarose by washing the solid gel slice twice with 2 volumes of 1× β-Agarase I Buffer on ice for 30 minutes each.
8) Remove the remaining buffer and melt the agarose by incubation at 68° C. for 10 minutes or until agarose is fully melted. Reduce temperature to 42 C and equilibrate solution at this temperature for 15 min.
   Note: If the temperature falls below 42° C. during the reaction time, even low melting point agarose will begin to congeal and be undigestable. β-Agarase I is quickly inactivated at temperatures above 45° C. Therefore, when working with large volumes, be sure to leave ample time for the molten agar to equilibrate to 42° C. and check temperature using a thermometer.
9) Incubate the molten agarose with 2 unit of β-Agarase I per 200 ul of molten agarose at 42° C. for 1 hour.
10) Adjust the salt concentration of the β-Agarase I treated solution for ethanol precipitation of DNA by adding 0.1 volume 0.3M sodium acetate, pH 5.2
11) Chill on ice for 10 minutes.
12) Centrifuge at max for 15 minutes to pellet any remaining undigested carbohydrates.
13) Remove the DNA-containing supernatant to a new tube. Precipitate with 2 volumes of ethanol
14) Mix thoroughly, incubate at −80 C for 15 min and centrifuge at max for 15 minutes.
15) Remove the supernatant, wash twice the pellet with 70% ethanol. Remove all ethanol and dry the pellet at room temperature.
16) Resuspend pellet in 100 ul Tris-low EDTA buffer.
17) Quantify DNA using QUBIT high sensitivity assay
18) To verify presence of mostly linear concatemers, digest library using mix of λexonuclease (ds exonuclease) and RecJf (ss exonuclease):
   10 ul library
   2.5 ul water
   2.5 ul 10λexonuclease reaction buffer
   5 ul λexonuclease
   5 ul RecJf exonuclease After mixing, split reaction and leave 12.5 ul on ice (undigested control)

Incubate 12.5 ul of the reaction mix at 37 C for 45 min.

Run both mixes on a 1% agarose e-gel side by side

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of this disclosure and these claims.

We claim:

1. A method for detecting spatial proximity relationships between nucleic acid sequences in a sample, comprising:
   providing a sample comprising nucleic acids;
   fragmenting the nucleic acids present in the sample, wherein the fragmented nucleic acids are less than 3 kb in size and have ends capable of joining to other fragmented nucleic acids;
   joining ends of fragmented nucleic acids to other ends of fragmented nucleic acids to create nucleic acid concatemers having a junction between each of two joined fragmented nucleic acids, and wherein the nucleic acid concatemers encode information about the proximity of nucleic acid sequences in the sample;
   isolating linear nucleic acid concatemers based on size from said concatemers having a junction between each of two joined fragmented nucleic acids, wherein linear concatemers greater than 3 kb in size are isolated;
   determining the sequences of the junctions in the linear nucleic acid concatemers; and
   generating a multidimensional contact map comprising at least one triplet contact based on the sequence of the junctions, thereby detecting spatial proximity contacts simultaneously between multiple nucleic acid sequences in the sample.

2. The method of claim 1, wherein the nucleic acids are held in a fixed position relative to one another by fixing the sample prior to use.

3. The method of claim 1, wherein determining the sequences of the junctions in the nucleic acid concatemers comprises nucleic acid sequencing.

4. The method of claim 1, wherein determining the sequences of the junctions in the nucleic acid concatemers comprises using a probe or a set of probes, wherein each probe specifically hybridizes to a junction both 5' and 3' of the site of the junction and spans the site of the junction.

5. The method of claim 1, wherein isolating the linear nucleic acid concatemers comprises isolating concatemers that are about 5-10 kb in length.

6. The method of claim 1, wherein the nucleic acid fragments are between about 100 to about 1000 bases in length.

7. The method of claim 1, wherein the fragmented nucleic acids are end repaired prior to joining.

8. The method of claim 1, wherein the sample is a sample of one or more cells.

9. The method of claim 8, further comprising lysing the one or more cells, isolating nuclei from the one or more cells, or lysing nuclei from the one or more cells.

10. The method of claim 1, wherein the sample is acellular.

11. The method of claim 1, wherein fragmenting the nucleic acids comprises fragmenting both DNA and RNA, and wherein the concatemers comprise both DNA and RNA sequences.

12. A method for diagnosing a disease or condition, the method comprising:
  detecting, in a sample, at least one junction that is indicative of a disease or condition, wherein detection of the at least one junction that is indicative of a disease or condition diagnoses the disease or condition, and wherein the at least one junction is detected using the method of claim 1.

\* \* \* \* \*